(12) United States Patent  (10) Patent No.: US 7,341,348 B2
Eagan  (45) Date of Patent: Mar. 11, 2008

(54) MOIRÉ ABERROMETER

(75) Inventor: Barry T. Eagan, Salt Lake City, UT (US)

(73) Assignee: Bausch & Lomb Incorporated, Rochester, NY (US)

( * ) Notice: Subject to any disclaimer, the term of this patent is extended or adjusted under 35 U.S.C. 154(b) by 798 days.

(21) Appl. No.: 10/397,099

(22) Filed: Mar. 25, 2003

(65) Prior Publication Data

US 2004/0189938 A1     Sep. 30, 2004

(51) Int. Cl.
*A61B 3/10*     (2006.01)
(52) U.S. Cl. ........................................ 351/221; 351/212
(58) Field of Classification Search ................ 351/211, 351/212, 221, 247; 356/124–127, 605, 618, 356/121; 250/201.9
See application file for complete search history.

(56) References Cited

U.S. PATENT DOCUMENTS

| | | | |
|---|---|---|---|
| 4,541,697 A | 9/1985 | Remijan | 351/211 |
| 4,670,646 A | 6/1987 | Spivey | 250/201 |
| 4,692,003 A | 9/1987 | Adachi et al. | 351/212 |
| 4,939,380 A | 7/1990 | Berger | 250/578.1 |
| 5,307,097 A | 4/1994 | Baker | 351/212 |
| 5,835,218 A | 11/1998 | Harding | 356/354 |
| 5,963,300 A | 10/1999 | Horwitz | 351/209 |
| 5,973,773 A | 10/1999 | Kobayashi | 356/124 |
| 6,439,720 B1 * | 8/2002 | Graves et al. | 351/211 |
| 6,634,750 B2 * | 10/2003 | Neal et al. | 351/211 |
| 6,702,806 B2 * | 3/2004 | Gray et al. | 606/5 |

FOREIGN PATENT DOCUMENTS

| | | |
|---|---|---|
| WO | 92/01417 | 2/1992 |
| WO | 97/04285 | 2/1997 |
| WO | 97/25590 | 7/1997 |

OTHER PUBLICATIONS

Rotlex website page showing Brass 2000, Jan. 27, 2003.
"Shadow moire and the use of flexible gratings to adapt to curved surfaces", by Martinez-Anton, et al., from NDT.net website, Jan. 27, 2003.
Chapters 6 and 7 from the book *The Physics of Moire Metrology*, by Kakfri et al., 1990.
"Automatic fringe detection algorithm used for moire deflectometry", by Servin et al., *Applied Optics*, vol. 29, No. 22, Aug. 1, 1990.
"Automatic processing in moire deflectometry by local fringe direction calculation", by Canabal et al., *Applied Optics*, vol. 37, No. 25, Sep. 1, 1998.

(Continued)

*Primary Examiner*—Alicia M Harrington

(57) ABSTRACT

An improved moiré deflectometer device for measuring a wavefront aberration of an optical system includes a light source for illuminating a surface area of the optical system, an optical relay system for directing scattered light to a deflectometer component that converts the wavefront into a moiré fringe pattern, a sensor/camera assembly for imaging and displaying the exit pupil of the optical system and the moiréfringe pattern, and a fringe pattern to calculate the wavefront aberration of the optical system, being improved by an illumination source for illuminating the exit pupil of the optical system; and an alignment system cooperating with the illumination source in such a manner to consistently and accurately align a measurement axis of the device to the optical system. An associated method is also disclosed.

34 Claims, 8 Drawing Sheets

OTHER PUBLICATIONS

"Diffraction effects in moire deflectometry", by Keren et al., *J. Optical Society of America*, vol. 2, No. 2, Feb. 1985.

"Double Frequency Grating Lateral Shear Interferometer", by Wyant, *Applied Optics*, vol. 12, No. 9, Sep. 1973.

"Fast Fourier transform, iteration, and least-squares-fit demodulation image processing for analysis of single-carrier fringe pattern", by Gu et al., *J. Optical Society of America*, vol. 12, No. 10, Oct. 1995.

"Fourier transform profilometry for the automatic measurement of 3-D object shapes", by Takeda et al., *Applied Optics*, vol. 22, No. 24, Dec. 15, 1983.

"Fourier-transform method of fringe-pattern analysis for computer-based topography and interferometry", by Takeda, et al., *J. Optical society of America*, vol. 72, No. 1, Jan. 1982.

"High resolution moire photography: application to dynamic stress analysis", by Huntley et al., *Optical Engineering*, vol. 28, No. 8, Aug. 1989.

"Interferogram analysis using Fourier transform techniques", by Roddier et al., *Applied Optics*, vol. 26, No. 9, May 1, 1987.

"An Interferometer Based on the Talbot Effect", by Lohmann et al., *Optics Communications*, vol. 2, No. 9, Feb. 1971.

"Lateral aberration measurements with a digital Talbot interferometer", by Takeda et al., *Applied Optics*, vol. 23, No. 11, Jun. 1, 1984.

"Local dioptric power matrix in a progressive addition lens", by Alonso et al., *Ophthal. Physiol. Opt.*, vol. 17, No. 6, pp. 522-529, 1997.

"Modified Fourier transform method for interferogram fringe pattern analysis", by Liu et al., *Applied Optics*, vol. 36, No. 25, Sep. 1, 1997.

"Phase measuring algorithm for extraction of isochromatics of photoelastic fringe patterns", by Quiroga et al., *Applied Optics*, vol. 36, No. 32, Nov. 10, 1997.

Chapter 14 from the book *Optical Shop Testing*, 2d ed., by Grievenkamp et al., 1992.

"Phase shifting for nonsinusoidal waveforms with phase-shift errors", by Hibino et al., *J. Optical society of America*, vol. 12, No. 4, Apr. 1995.

"Phase-shifting Moire deflectometry", by Pfeifer et al., *Optik*, 98, No. 4 (1995).

"Fourier transform method for automatic processing of moire defectograms", by Quiroga et al., *Optical Engineering*, vol. 38(6), pp. 974-982, Jun. 1999.

"Refractive power mapping of progressive power lenses using Talbot interferometry and digital image processing", by Nakano et al., *Optics & Laser Technology*, vol. 22, No. 3, 1990.

"Ronchi test with a square grid", by Cordero-Davila, et al., *Applied Optics*, vol. 37, No. 4, Feb. 1, 1998.

"Shearing Interferometer Using the Grating as the Beam Splitter", by Yokozeki et al., *Applied Optics*, vol. 10, No. 7, Jul. 1971.

\* cited by examiner

MOIRÉ ABERROMETER

BACKGROUND OF THE INVENTION

1. Field of the Invention

The invention is primarily directed to ophthalmic wavefront sensing apparatus and methods and more particularly to a wavefront sensor apparatus and method based upon the principles of moiré deflectometry.

2. Description of Related Art

The measurement of wavefront aberrations of the eye up to the $10^{th}$ Zernike order continues to find increasing application in the field of ophthalmology, particularly in relation to refractive surgical procedures such as LASIK, LASEK, PRK, and others. It is no longer adequate to merely measure the topology of the cornea to determine how to best re-shape a person's cornea for vision correction. And while corneal topography systems used in combination with pachymetry devices and ray-tracing techniques can provide a wealth of information about a person's eye and vision problems, aberrometry provides on its own, unique information about the visual defects of the entire optical system of the eye. Wavefront sensing has application ranging from objective refraction measurement for traditional correction of defocus and astigmatism to contributing to the creation of customized ophthalmic lenses (e.g., contact lenses, IOLs, etc.) and customized laser ablation treatments which have the potential to provide vision improvement up to the theoretical limit of the human eye.

Aberrometers and the principles upon which they operate can generally be classified into four types: (1) out-going (e.g., Hartmann-Shack); (2) double-pass (e.g., slit skioscopy); (3) in-going adjustable (e.g., spatially resolved refractometer); and (4) retinal image aberrometry (e.g., Tscherning, Tracey). In the current commercial environment, Hartmann-Shack wavefront sensor-based aberrometry is most prevalent. However, Hartmann-Shack, as well as the other wavefront measuring principles embodied in the various commercially available devices each have relative identifiable advantages and disadvantages. The interested reader is directed to the *Journal of Refractive Surgery*, Vol. 16, No. 5 (September/October 2000), which provides a thorough review of ophthalmic aberrometry based upon the proceedings of the First International Congress of Wavefront Sensing and Aberration-Free Refractive Correction.

Ophthalmic wavefront sensing and analysis is by no means limited by the categories described above. Researchers in the field of psychophysics, such as Smirnov in the 1960's, Howland in the mid-80's, and Liang and Williams in the late 80's through the mid-90's, to name just a few, employed various optical principles to acquire and analyze ocular aberration data. Likewise, a great deal of know-how for ophthalmic applications has been transferred from the fields of astronomy, strategic defense initiatives, and optical lens testing.

In International Patent Application Publication WO 92/01417, Horwitz discussed automated binocular vision measurement and correction relying on moiré fringe generation and analysis, commonly known as moiré deflectometry. The publication described a binocular apparatus allegedly having the capability to measure up to 256 aberrations of the eye, and the application of this technology to the design and manufacture of customized ophthalmic lenses and laser refractive surgery. In 1999, Horwitz U.S. Pat. No. 5,963,300 disclosed an ocular biometer based in part upon moiré deflectometry and included a limited teaching of Fourier analysis for providing wavefront aberration information. Notwithstanding the issuance of the '300 patent, it appeared that application of the technology to ocular wavefront sensing needed something more, which apparently was provided, at least in part, by Quiroga et al., Fourier transform method for automatic processing of moiré deflectograms, *Opt. Eng.* 38(6) 974-982 (June 1999).

The measurement limitations of Hartmann-Shack-type aberrometers and their size, cost, and complexity are issues well appreciated by those skilled in the art. The inventor has recognized that improvements to the apparatus and methods of moiré deflectometry could advantageously address many of the issues associated with current aberrometer technology. Accordingly, the instant specification discloses improved moiré deflectometry apparatus and methods believed by the inventor to provide wavefront measurements having better resolution, higher reliability, and accurate analysis capability that is simpler, less costly, and more robust than Hartmann-Shack and other commercially available ocular aberrometer systems.

SUMMARY OF THE INVENTION

An embodiment of the invention is directed to a device for measuring a wavefront aberration of an optical system, preferably living human eyes and test objects intended for calibration purposes. The device embodied by the invention is based upon the principle of moiré deflectometry. A moiré deflectometer includes a light source that is used to illuminate a selected surface area of the optical system under test, an optical relay system for directing the light source illumination scattered from the surface area of the optical system to a deflectometer which converts the outgoing wavefront from the optical system into a moiré fringe pattern, a sensor/camera assembly that detects the moiré fringe pattern, and a fringe pattern analyzer used to calculate the wavefront aberration of the optical system, wherein an improvement to the device is characterized by an illumination source that is used to illuminate an exit pupil of the optical system, and an alignment system that provides the ability to consistently and accurately align the optical system under test to a defined measurement axis of the device. Preferred aspects of the instant embodiment include the following: The light source emits coherent light in the form of a collimated beam having a cross-sectional diameter at an anterior surface of the optical system (e.g., tear film/cornea) larger than a diffraction limited size up to about 1 mm. The propagation axis of the collimated beam at the anterior surface is parallelly displaced from the optical axis of the optical system by about 1 mm. A preferred wavelength is approximately 780 nm. The deflectometer includes a first square grid having mutually orthogonal, periodic gridlines and a second, preferably identical square grid. The two square grids are located on the optical axis with the first grid's gridlines aligned along the x- and y-axes in an x-y plane of a Cartesian coordinate system corresponding to the alignment of the detector in the sensor/camera assembly. The second square grid is located at one or more Talbot distances downstream of the first square grid and is rotated in the x-y plane with respect to the first grid at an angle θ between, but not including, 0° to 90°. The sensor/camera assembly preferably is a CCD detector camera with associated lenses for focusing the moiré fringe pattern onto the detector. The illumination source is preferably a controllable far IR source providing uniform illumination of the exit pupil of the optical system during an alignment phase of the wavefront measurement and being capable of not illuminating the exit pupil of the optical system during an acquisition phase of the wavefront measurement. The device further includes an alignment system preferably having a software-generated cross-hair indicia in the camera display to provide identification of a centering position of the exit pupil along the measurement axis of the device.

The present invention will become more readily apparent from the detailed description to follow. However, it should be understood that the detailed description and specific examples, while indicating the preferred embodiments of the invention, are given by way of illustration only, since various changes and modifications within the spirit and scope of the invention will become apparent to those skilled in the art based upon the description and drawings herein and the appended claims.

DETAILED DESCRIPTION OF A PREFERRED EMBODIMENT OF THE INVENTION

Figure 1:
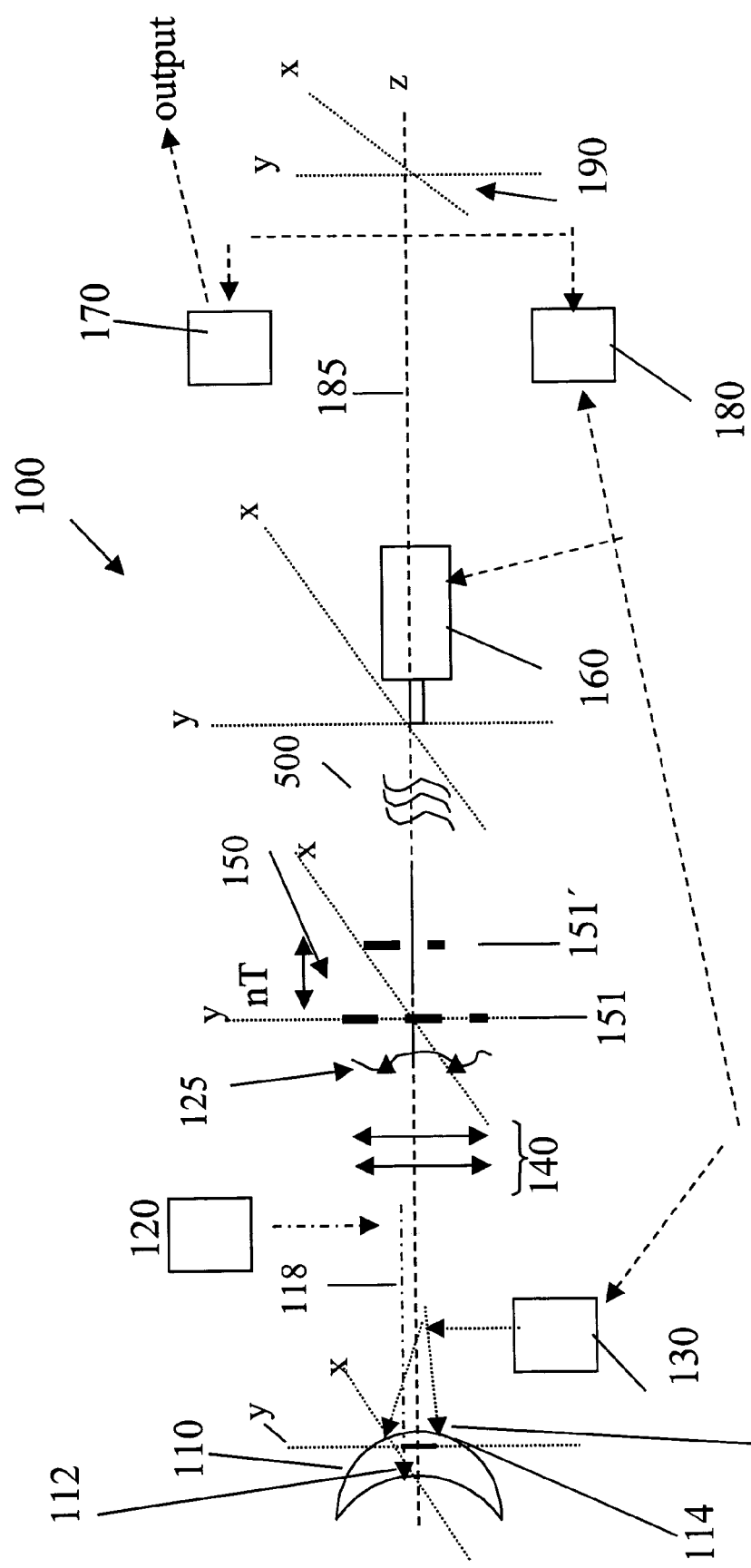
FIG. 1 is a diagrammatic illustration of a moiré deflectometer according to an embodiment of the invention.

An embodiment of the moiré wavefront sensor apparatus 100 according to the invention is illustrated in FIG. 1. The device, in essence a moiré deflectometer, measures and analyzes wavefront aberrations of an optical system 110. Optical systems of interest include living human eyes and test objects for calibration purposes, however, the invention is not limited to measurement of these objects. The system 110 operates as a single pass wavefront measuring system as that term is understood in the art. That is, a point source of light of an appropriate spot diameter is created on a posterior diffuse surface 112 of the optical system; i.e., the retina. The posterior surface 112 will diffusely reflect and scatter the small spot of light through and away from the optical system 110 in the form of a wavefront 125.

Figure 2:
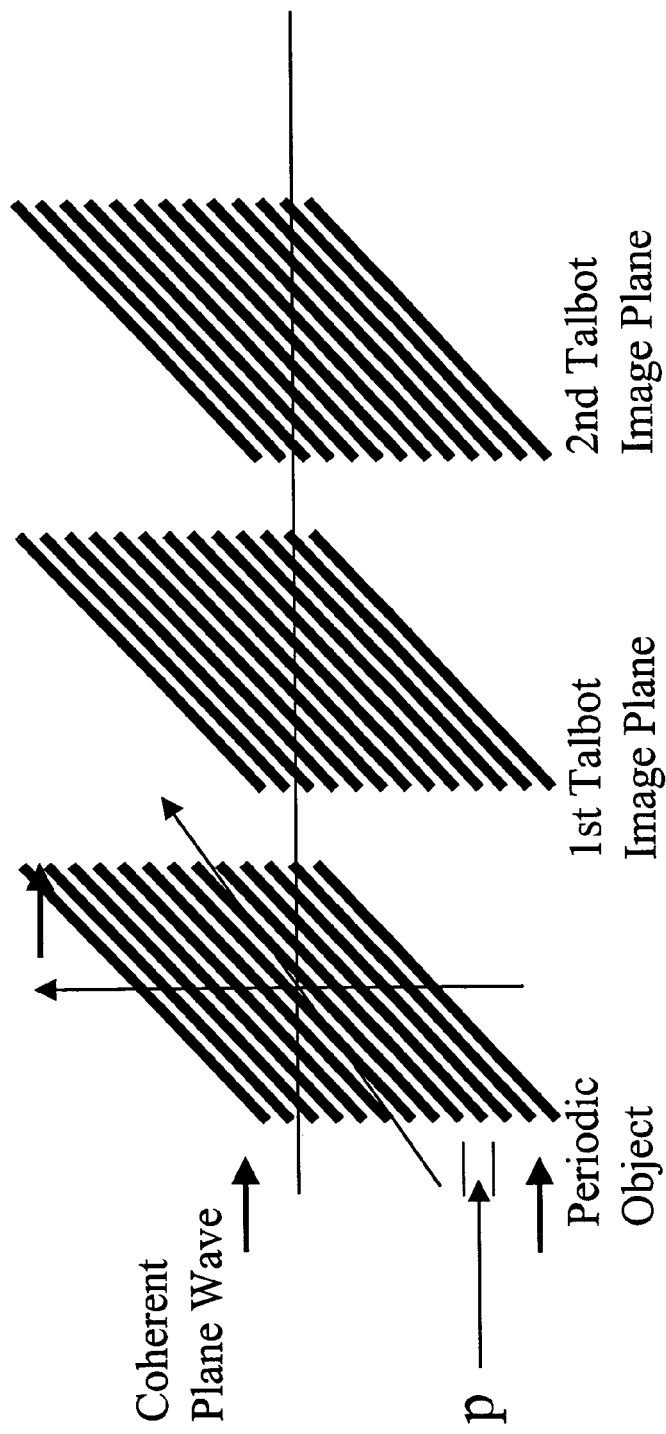
FIG. 2 illustrates the principle of unaberrated Talbot imaging of a periodic object.
Figure 3:
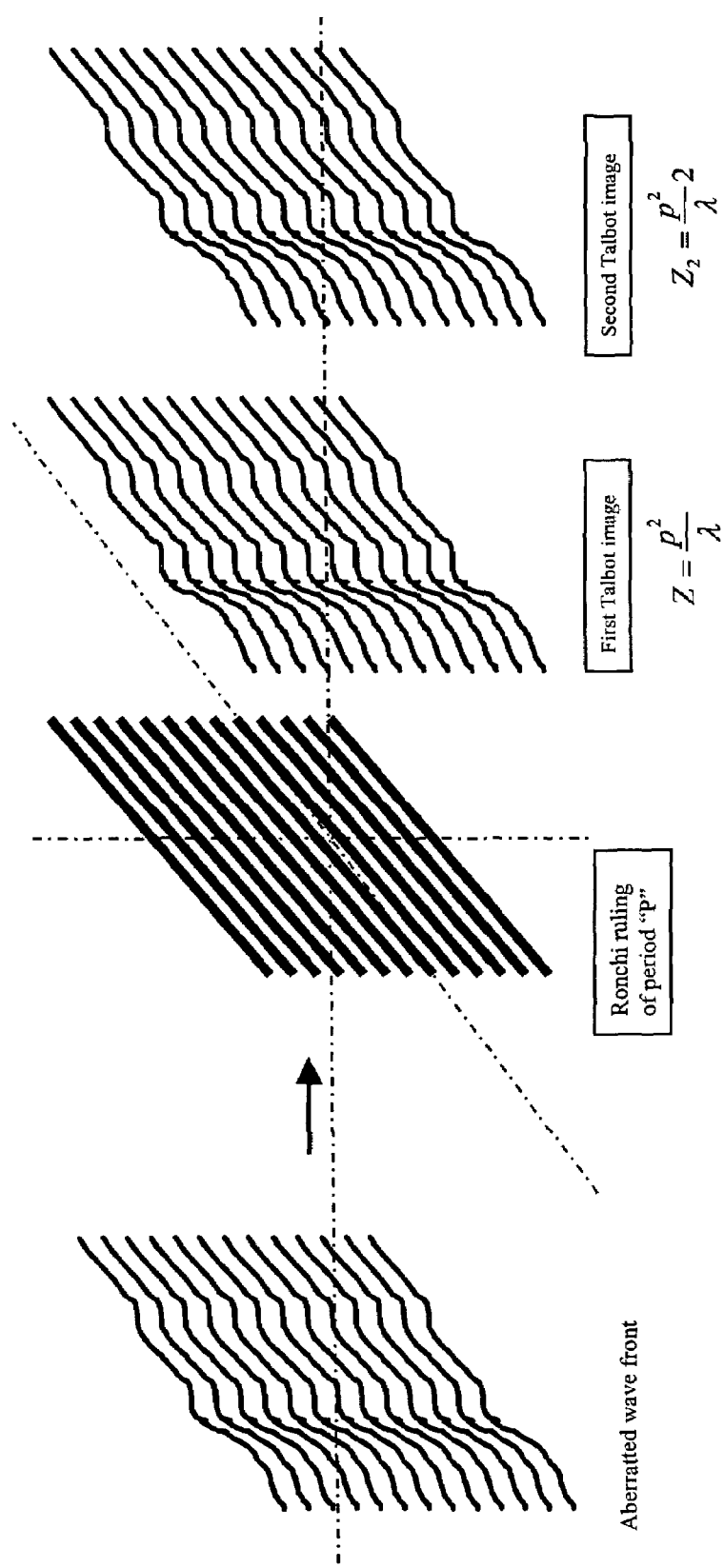
FIG. 3 illustrates aberrated Talbot imaging of a periodic object.
Figure 4:
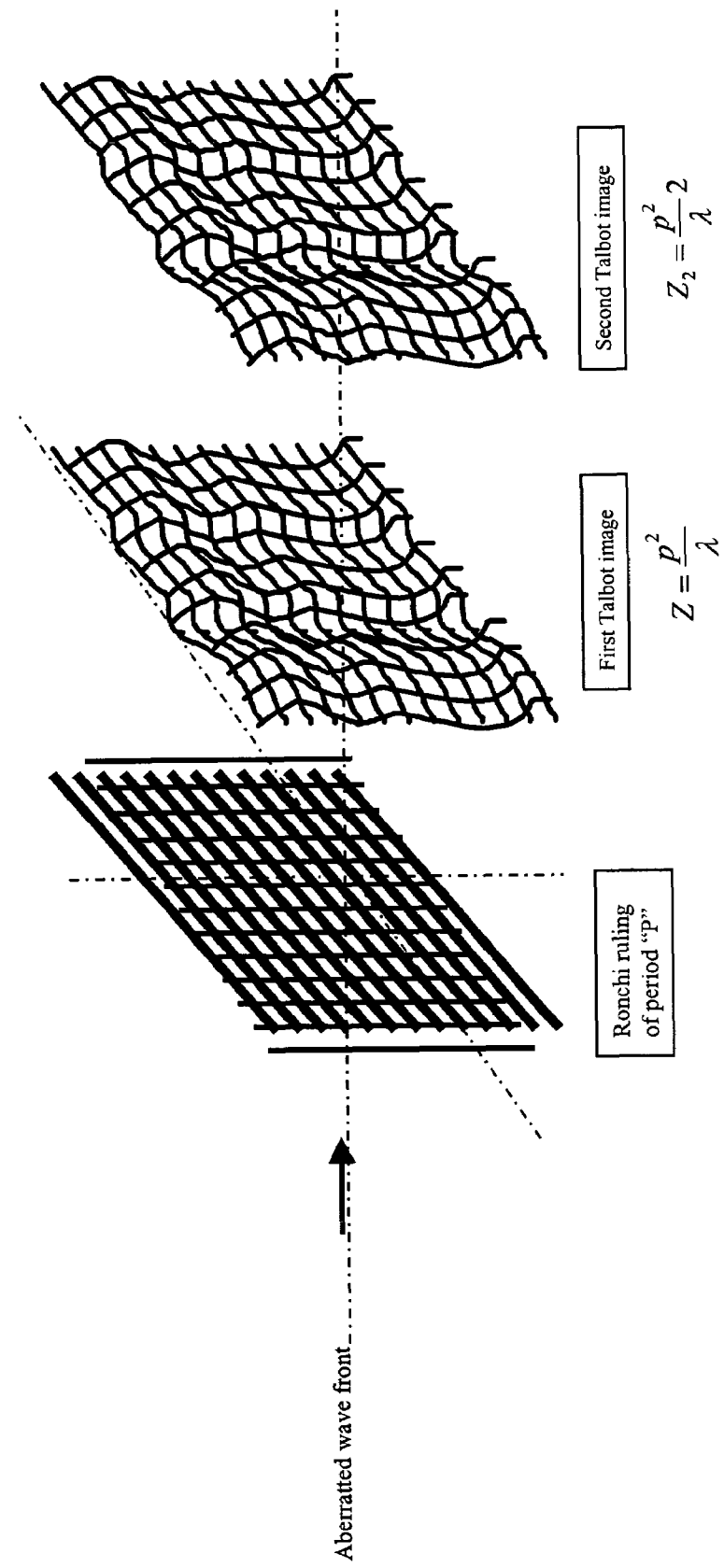
FIG. 4 illustrates aberrated Talbot imaging of a crossed square periodic object.
Figure 5:
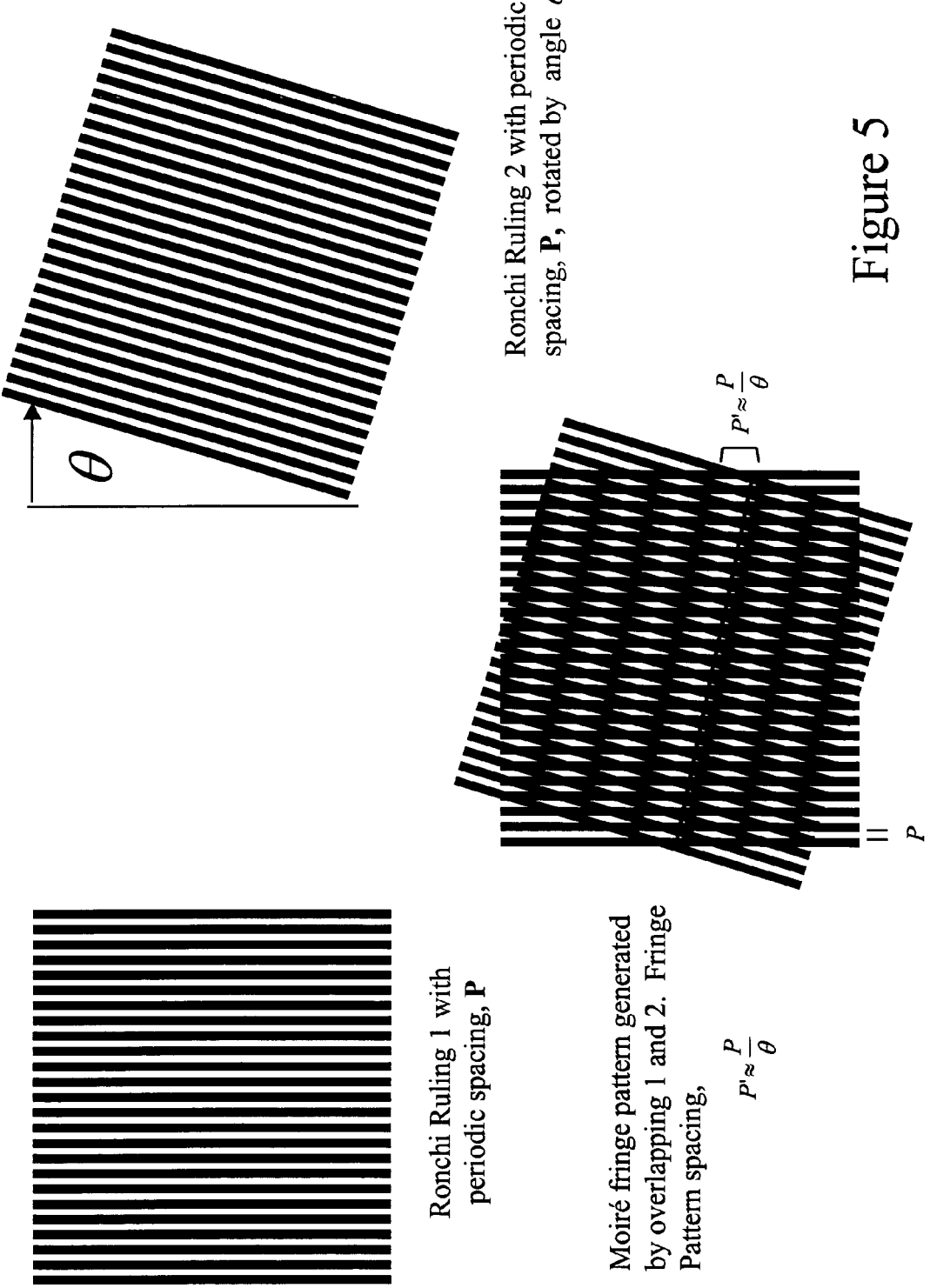
FIG. 5 illustrates a moiré effect due to a relative rotation between a first periodic object and a second periodic object.
Figure 6:
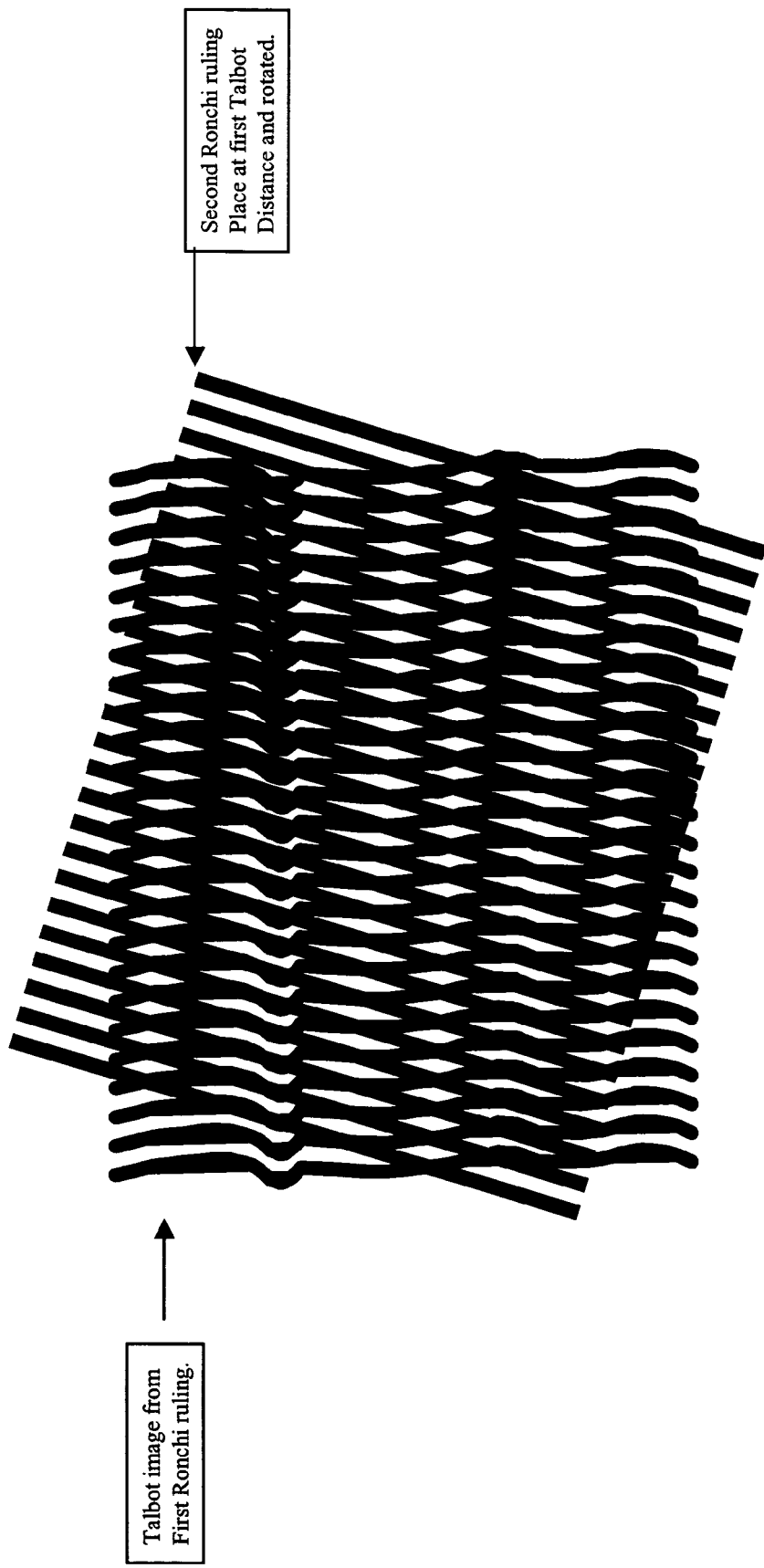
FIG. 6 illustrates a moiré effect due to the superposition of a distorted Talbot image and a second periodic object.

The fundamental principle of operation of the apparatus disclosed herein is based on Talbot imaging. Talbot imaging is a diffraction phenomenon that occurs with a periodic object, for example, a transmission grating. Under proper illumination by a plane wave, perfect replicas of the object appear at fixed distances called Talbot planes as illustrated in FIG. 2. The locations of the Talbot planes, $Z_j$, depend on the period, p, of the object and the wavelength, $\lambda$, of light according to the relationship $Z_j = p^2 j/\lambda$. If the illuminating wavefront is aberrated, the Talbot images are distorted as illustrated in FIG. 3. The amount of distortion depends upon the wavefront slope in the direction perpendicular to the grid orientation of the object. Crossed gratings, as illustrated in FIG. 4 and described in detail below, can be used to recover the wavefront slope in two orthogonal directions. For large grating periods, the distorted Talbot images can be captured and conveniently analyzed. To increase resolution, however, finer grating periods can be used by positioning a second grating at one of the subsequent Talbot planes and rotating it in the plane of the first grating object. This gives rise to a moiré effect as illustrated in FIG. 5. The superposition of the distorted Talbot image and the second grating produces a moiré fringe pattern. The shape of the moiré pattern is related to the slope of the wavefront, illustrated in FIG. 6.

The apparatus 100 includes a light source 120 suitable for illuminating a selected surface area 112 of the optical system 110, an optical relay system 140 for directing the light scattered from the surface area of the optical system to a deflectometer 150, which produces a moiré fringe pattern 500 from the outgoing wavefront 125. A sensor/camera assembly 160 is provided and is aligned in such a manner to capture the moiré fringe pattern which can be analyzed by a fringe pattern analyzer 170 (e.g., programmed personal computer) to provide wavefront aberration information for a variety of advantageous purposes related to vision measurement and correction methods and apparatus. The device 100 further includes an illumination source 130 for providing imaging illumination of an exit pupil 114 of the optical system, and an alignment system 180 that facilitates consistent alignment and measurement related to a coordinate system 190 associated with the device as shown. The device has an orientation with respect to a Cartesian coordinate system as illustrated in FIG. 1; i.e., the z-axis 185 represents the measurement axis of the device, and the various lenses, gratings, and detector/camera lie in x-y planes aligned to the x- and y-axes.

In a preferred embodiment according to the invention, the optical system 110 is a living human eye and the surface area of the posterior surface 112 is a foveal area of the retinal surface of the eye. A light source 120 emits illumination to illuminate the selected surface area of the optical system in the form of substantially a point source of light. The light source 120 can be any suitable source known to those skilled in the art that emits coherent light having a wavelength preferably in the near IR spectrum. The wavelength range is preferably between about 770 nm to 790 nm, and most preferably about 780 nm. The illumination 121 is conditioned either internally or externally of the light source 120 by well-known means to be in the form of a collimated beam of light having a cross-sectional beam diameter ranging from slightly greater than a diffraction limited amount up to about 1 mm at or proximate an anterior surface 116 of the optical system. In a preferred ophthalmic embodiment, the collimated light input to the eye will have a beam diameter between about 300 microns to about 1000 microns, and more preferably between about 600 and 1000 microns, at the cornea/tear film surface of the eye. The collimated input beam 121 has a propagation axis 118 that preferably is displaced parallel to the system z-axis 185 by a distance of approximately 1 mm. Displacement of the in-going beam eliminates specular reflection; for example, the first Purkinje image, from the corneal surface and reflections from other surfaces of the optical system that might obscure the weak retinal reflection containing the wavefront information to be measured. It will be appreciated by those skilled in the art that a small displacement and small beam diameter at the corneal surface will reduce corneal-induced aberration of the in-going beam.

It is well known that in an emmetropic eye, a plane wavefront input to the eye will focus to a point on the retinal surface. A near-sighted or far-sighted eye, however, will focus the same input wavefront at points in front of or behind the retina, respectively, such that the light spot on the retinal surface will no longer be a point source of suitable size for convenient or even possible measurement of the wavefront error. The small diameter input beam as disclosed herein, referred to as direct injection due to elimination of the need for any refracting components in the beam path between the source and the object, has been demonstrated to obviate the problems of near- and far-sighted defocus without the use of external focussing and polarizing optics or beam path length adjustment. A preferred dioptric measurement range is between −12 to +6 diopters and, more preferably, between ±20D. Direct injection of the illumination light is described in co-pending patent application Ser. No. 10/027377 entitled ABERROMETER ILLUMINATION APPARATUS AND METHOD, filed on Dec. 21, 2001, which is commonly assigned to the instant applicant. The interested reader is also directed to Williams et al. U.S. Pat. No. 6,264,328 for a detailed discussion of a wavefront sensor with off-axis illumination. Both of these references are fully incorporated by reference herein to the extent allowed by applicable patent laws and rules.

The retinal surface of the eye, or posterior surface of the optical system, diffusely reflects and scatters the point source of light forming an aberrated wavefront 125 traveling away from the optical system. A relay system 140 well known to those skilled in the art directs the propagation of the wavefront 125 to a deflectometer 150, described below.

Figure 7:
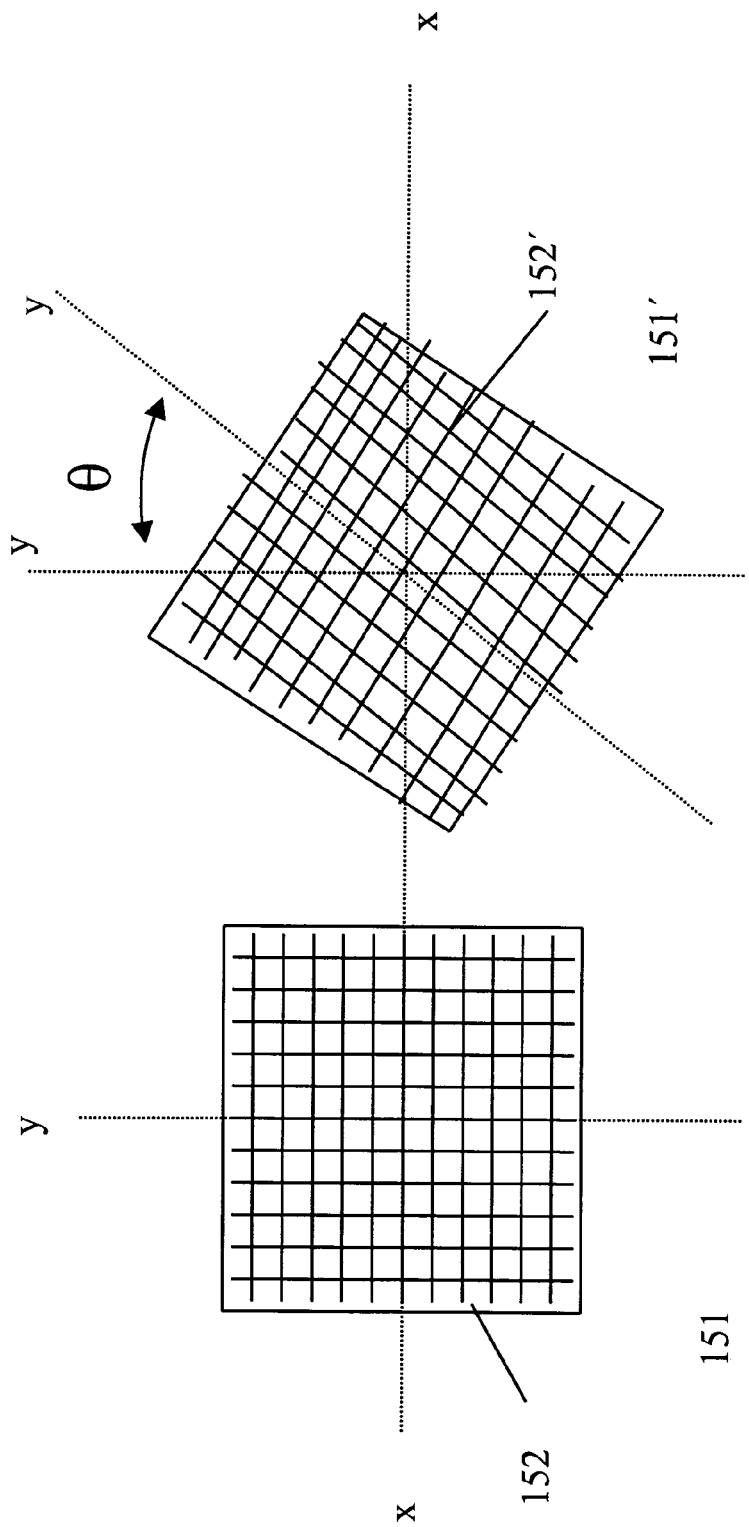
FIG. 7 is a diagrammatic illustration of the relative rotation between two crossed grids in an x-y plane according to an embodiment of the invention.

The deflectometer 150 is composed of two components 151, 151'. The components each have a grid of equally periodic orthogonal gridlines 152, 152'; e.g., each component is a crossed square-grating reticle, as shown in FIG. 7 (referred to herein as first and second square grids 151, 151'). The gridlines 152 (152') preferably are laser-etched into a glass substrate, but are not so limited in construction according to the invention. The square grids 151, 151' preferably are identical. The first square grid 151 is positioned along the measurement axis 185 to intercept the wavefront 125 traveling from left to right as shown in FIG. 1. As illustrated in greater detail in FIG. 4, first square grid 151 is aligned in the x-y plane such that the horizontal gridlines are parallel to the x-axis and the vertical gridlines are parallel to the y-axis of the device coordinate system. It is most preferred that the detector portion of the sensor/camera assembly 160 also be in substantially identical alignment in the x-y plane with the first square grid 151. Failure to couple these alignments makes it difficult, if not impossible, to decouple the measured aberrations along the x- and y-axes, which is preferable for ophthalmic wavefront sensing applications. The coalignment described immediately above can be a structurally fixed characteristic of the device. The second square grid 151' is displaced downstream of the first square grid along the z-axis as shown in FIG. 1 by a distance nT where T is the Talbot distance and n is an integer. In a preferred embodiment, n=1. In the device, the second square grid 151' is selectively and fixedly tilted in the x-y plane with respect to the first component by an angle, θ, where 0°<θ<90°. It has been shown by Quiroga et al., *Fourier transform method for automatic processing of moiré deflectograms*, Opt. Eng. 38(6) 974-982 (June 1999), incorporated herein by reference in its entirety to the fullest allowable extent, that the typical arrangement of the gratings in which they are rotated symmetrically by θ/2 and −θ/2 with respect to the reference axis, is not well suited to completely separate the x and y components of the wavefront gradient. The results obtained for the deflections are, $$\hat{\varphi}_x = \varphi_x \cos\frac{\theta}{2} + \varphi_y \sin\frac{\theta}{2} \text{ and } \hat{\varphi}_y = \varphi_y \cos\frac{\theta}{2} + \varphi_y \sin\frac{\theta}{2}.$$

These equations indicate that with the standard symmetrical arrangements for the grids, one cannot get complete decoupling of the deflections in the x and y directions. When θ=0, the deflections are decoupled but there is no spatial carrier required for a Fourier analysis of the fringe output. The largest possible spatial carrier is preferred. Thus, θ should be large enough that sin $$\frac{\theta}{2} \neq 0,$$

with $\theta_{max}$ depending upon the size of the CCD array and on the size of the grid spacing, P, since the amplification factor P'=P/θ. If θ gets too large, it may be difficult to image the fringes on the CCD array. If θ is too small, the spatial carrier is jeopardized. The reader interested in a more thorough discussion of moiré deflectometers and analysis is directed to the text by Kafri and Glatt entitled *The Physics of Moiré Metrology*, John Wiley & Sons, New York (1990), which is herein incorporated by reference in its entirety to the fullest allowable extent.

A fringe pattern sensor/camera assembly 160 preferably comprising a CCD detector and camera is provided, in part, to detect the moiré fringes and transmit this data to a fringe analyzer 170. The sensor/camera assembly 160 is also used to image and display the exit pupil of the optical system; i.e., the eye's pupil. In this regard, the device 100 further includes an illumination source 130 and a cooperatively engaged alignment system 180. Light emitted by the illumination source 130 should uniformly illuminate the exit pupil plane. It is preferably in the far IR spectrum in a wavelength range that will not cause a change in pupil size due to light response, but at the same time is detectable by the camera for imaging the exit pupil. A wavelength of about 880 nm has been shown to be effective, but other wavelengths can be used as those skilled in the art will appreciate. In operation, the illumination source will be in an illuminating mode (on) during the alignment of the patient's eye. While the wavefront measurement is being made, referred to as the measurement mode, the illumination source will be in a non-illuminating mode (off, or otherwise blocked from illuminating the eye). In an exemplary embodiment, the illumination source is in the form of a full or partial ring of LEDs suitably positioned to evenly illuminate the exit pupil plane.

Figure 8:
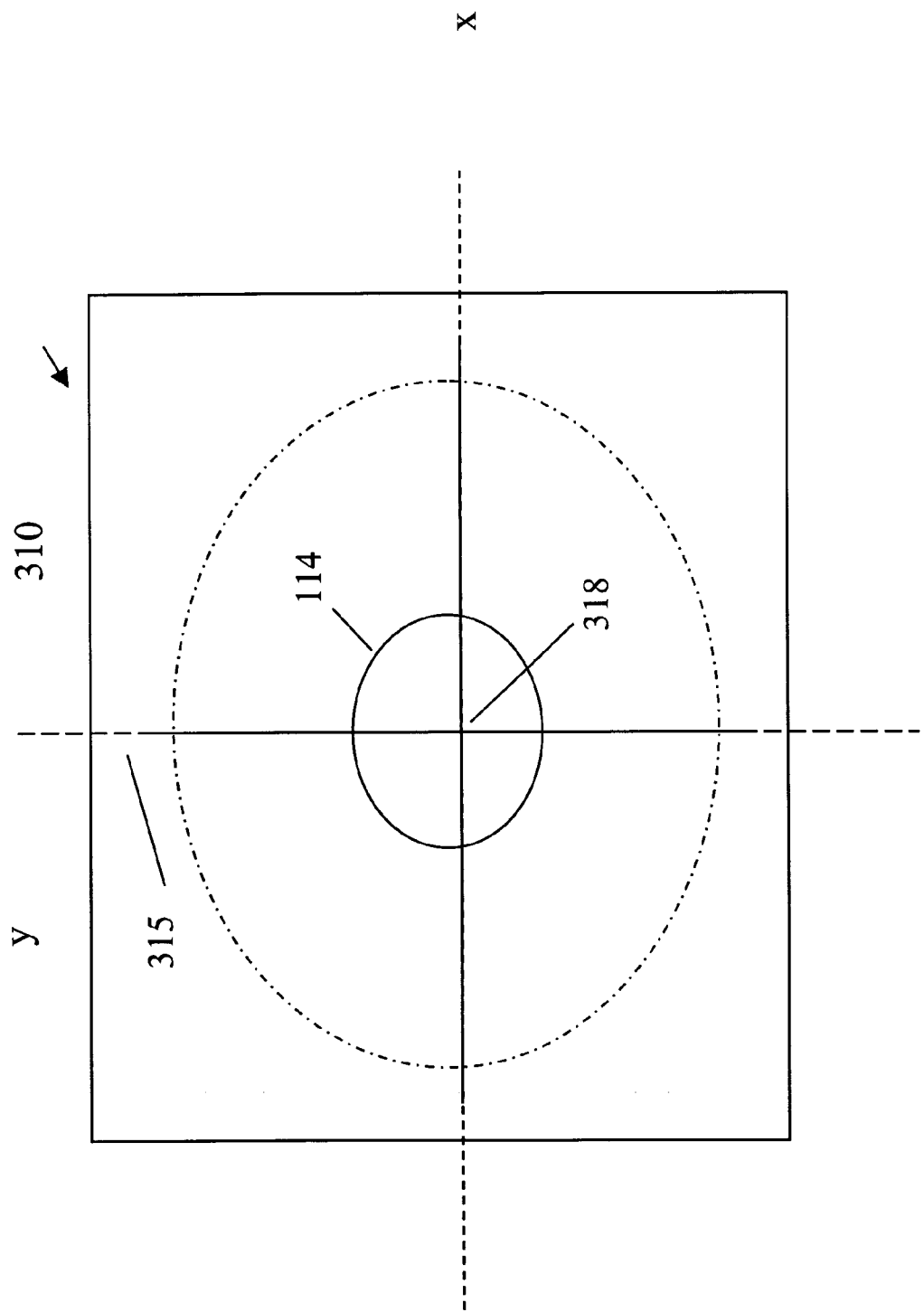
FIG. 8 is a diagrammatic illustration of a camera image of an exit pupil of an optical system under test aligned with cross hairs according to an embodiment of the invention.

In order to accurately and consistently measure wavefront aberrations, there must be accurate and consistent alignment between the measurement axis 185 of the device 100 and the eye being measured. If the exit pupil of the optical system is not properly centered and aligned, the image of the exit pupil may appear as a normally round image, however it may unknowingly be vignetted due to misalignment. Failure to consistently center and align the device may result in different and erroneous wavefront measurements from the eye being measured each time a measurement is obtained. As part of the alignment system 180 and related procedure, a cross-hair indicia 315 as illustrated in FIG. 8 is provided to assist in centering the exit pupil 114 to the measurement axis 185 of the device. The pupil can be viewed directly through the camera 160. In a preferred embodiment, the cross-hair indicia is implemented via software and displayed with the pupil image of the eye, allowing the user to focus on the pupil center repeatedly. Other alignment schemes are possible. The visual axis, for example, could be used for alignment rather than the pupil center. The important point is to consistently align the exit pupil each and every time a measurement is made.

The optics of the device (reticles, lenses, detectors, etc.) should be sufficient to preferably measure an exit pupil having up to an 8 mm diameter. This size represents the substantial pupil diameter for higher order aberration measurement and correction via custom lenses or refractive surgery (e.g., custom LASIK, LASEK, PRK, etc.) Larger diameter measurement capability may be desirable. A dynamic measurement range of +20 diopters is preferable.

A fringe pattern analyzer 170 is cooperatively engaged with the sensor 160 and is programmed to calculate the aberrations of the wavefront based upon the analysis of the moiré fringes detected. An outline of the moiré fringe pattern (Talbot interferogram, shadow pattern) analysis procedure for wavefront aberration calculation was presented in Horwitz U.S. Pat. No. 5,963,300, incorporated herein by reference in its entirety to the fullest allowed extent. In essence, the analysis comprised the steps of detecting the fringe (moiré, Talbot, Fresnel, shadow, etc.) pattern and digitizing it; converting the digital image from the spatial domain to the spatial frequency domain; determining the predominant harmonics; correlating the predominant harmonics to the wavefront figure in defined axes; calculating a three-dimensional optical domain wavefront figure; and analyzing the resulting measurements. An elegant description of a technique for analysis of moiré deflectograms is presented by Quiroga et al., id. A person skilled in the art could use the Quiroga et al. teaching to develop the appropriate software to extract the wavefront information from the phase information in the deflectogram.

The wavefront aberration analysis can be expressed in the form of Zernike polynomials which can be used to program lathes or other devices for the design and manufacture of custom contact lenses, custom IOLs, and the like, and to develop ablation patterns used in laser refractive surgery, as known by those skilled in the art.

Since the device as described herein can measure the decoupled wavefront aberration from defocus (second-order) up past fifth-order, the device has another advantageous application as an objective phoropter. A binocular device could also be implemented based upon the principles disclosed herein. Binocular pupilometry is the preferred way to measure pupil diameter since the behavior of both pupils is coupled.

While various advantageous embodiments have been chosen to illustrate the invention, it will be understood by those skilled in the art that changes and modifications can be made therein without departing from the scope of the invention as defined in the appended claims.

I claim:

1. A device for measuring a wavefront aberration of an ocular system, comprising:
   an aberration measurement light source suitable to illuminate a retinal surface of the ocular system;
   an optical relay system for directing the measurement light source illumination scattered from the retinal surface of the ocular system to a deflectometer component, wherein said deflectometer component adapts a wavefront from the optical system into a Moiré fringe pattern;
   a sensor/camera assembly adapted to image and display an exit pupil of the ocular system and the Moiré fringe pattern;
   an illumination source for illuminating the exit pupil of the optical system cooperating with the sensor/camera assembly for imaging and displaying the exit pupil and the Moiré fringe pattern;
   an alignment system cooperating with the illumination source in such a manner to consistently align a selected measurement axis of the device to the ocular system; and
   a fringe pattern analyzer adapted to calculate the wavefront aberration of the ocular system.

2. The device of claim 1, wherein the light from the light source is coherent light.

3. The device of claim 1, wherein the light from the light source is in the form of a collimated beam having a cross sectional diameter greater than a diffraction limited amount up to about 1 mm prior to illuminating the selected surface area of the optical system.

4. The device of claim 3, wherein the cross sectional diameter is between about 300 µ to 600µ.

5. The device of claim 1, wherein the light source illumination has an in-going propagation axis that is displaced from a centered optical axis of the optical system.

6. The device of claim 5, wherein the displacement is about 1 mm.

7. The device of claim 1, wherein the light source illumination has a wavelength in the near IR spectrum.

8. The device of claim 7, wherein the wavelength is in a range between about 770 nm to 790 nm.

9. The device of claim 8, wherein the wavelength is about 780 nm.

10. The device of claim 1, wherein the deflectometer comprises a first square grid having grid lines that are equally periodic in orthogonal directions, said grid being in fixed alignment with the sensor such that said orthogonal grid lines and a horizontal axis and vertical axis of the sensor are aligned to an x- and y-axes of a reference coordinate system of the device, and further comprising a second square grid that is substantially identical to the first square grid, wherein said first and second grids are located along a z-axis of the reference coordinate system at a separation distance, nT, where n is an integer equal to or greater than one and T is a Talbot distance, further wherein the second grid is rotated in the x-y plane with respect to the first grid at an angle, θ, where $0°<θ<90°$.

11. The device of claim 10, wherein $1°\leq θ \leq 10°$.

12. The device of claim 10, wherein the deflectometer is a glass material having laser-etched grid lines.

13. The device of claim 10, wherein the first and second grids are identical crossed pairs of Ronchi rulings.

14. The device of claim 1, wherein the sensor comprises a CCD camera.

15. The device of claim 1, wherein the illumination source for illuminating the exit pupil of the optical system has a wavelength in the far IR spectrum.

16. The device of claim 15, wherein the wavelength is in a range between about 800 nm to 900 nm.

17. The device of claim 16, wherein the wavelength is about 880 nm.

18. The device of claim 1, wherein the illumination source has an illuminating mode and a non-illuminating mode.

19. The device of claim 18, wherein the illumination source is in an ON-illuminating mode during an alignment phase and wherein the illumination source is in an OFF-non illuminating mode during a measurement phase.

20. The device of claim 1, wherein the illumination source is in the form of a ring of light emitting devices suitably positioned to uniformly illuminate the exit pupil.

21. The device of claim 1, wherein the alignment system comprises a cross-hair indicia to identify a centering position of the exit pupil on the cross-hair.

22. The device of claim 21, wherein the cross-hair indicia is a software implemented indicia.

23. The device of claim 1, wherein the fringe pattern analyzer is a component adapted to implement a software-driven Fourier transform analysis of the Moiré fringe pattern.

24. The device of claim 1, wherein the optical system is an eye, wherein the selected surface area is a foveal region of the retinal surface of the eye.

25. The device of claim 1, wherein the selected measurement axis is aligned to a center of the exit pupil.

26. The device of claim 1, wherein the selected measurement axis is aligned with a visual axis of the ocular system.

27. A method for measuring a wavefront aberration of an optical system using a moiré deflectometer device, comprising the steps of:

provided said device including a light source, a fringe pattern analyzer, an alignment system, and a deflectometer component comprising first and second square grids, wherein said first square grid has gridlines that are equally periodic in orthogonal directions, said first square grid being in fixed alignment with the sensor such that said orthogonal gridlines and a horizontal axis and vertical axis of the sensor are aligned to an x- and y-axis of a reference coordinate system of the device, and further wherein said second square grid is located downstream of the first square grid a distance, nT, where n is an integer equal to or greater than one and T is a Talbot distance, the second grid being fixedly rotated in the x-y plane with respect to the first grid at an angle, $\theta$, where $0° < \theta \leq 90°$;

uniformly illuminating an exit pupil of the optical system with light from the illumination source;

obtaining an image of the exit pupil including an alignment indicia;

consistently aligning the exit pupil with respect to the alignment indicia each time a wavefront measurement is to be made;

illuminating a selected diffusely reflecting surface region of the optical system with an appropriately sized spot of light provided by the light source; and obtaining wavefront aberration data.

28. The method of claim 27, wherein the step of uniformly illuminating the exit pupil comprises using a ring, or at least a part thereof, of light emitting sources.

29. The method of claim 27, wherein the step of uniformly illuminating the exit pupil comprises using light having a wavelength in a range of 800-900 nm.

30. The method of claim 27, wherein the step of uniformly illuminating the exit pupil comprises using light having a wavelength of about 880 nm.

31. The method of claim 27, wherein the step of consistently aligning the exit pupil comprises aligning a center of the exit pupil to a measurement axis of the device.

32. The method of claim 27, wherein the step of consistently aligning the exit pupil comprises aligning a visual axis through the exit pupil to a measurement axis of the device.

33. The method of claim 27, wherein the step of illuminating a selected diffusely reflecting surface region comprises directly injecting a collimated, coherent beam into the optical system.

34. The method of claim 27, wherein the beam has a diameter between about 600 to 1000µ.

* * * * *